(12) United States Patent
Okubo et al.

(10) Patent No.: US 6,360,584 B1
(45) Date of Patent: Mar. 26, 2002

(54) DEVICES FOR MEASURING GASES WITH ODORS

(75) Inventors: Kunihiko Okubo, Shiga; Keiso Kawamoto, Kyoto; Motoo Kinoshita, Kyoto; Hiroshi Nakano, Kyoto; Jun-ichi Kita, Kyoto; Mitsuyoshi Yoshii, Osaka; Hisamitsu Akamaru, Kyoto, all of (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/438,442

(22) Filed: Nov. 12, 1999

(30) Foreign Application Priority Data

Nov. 16, 1998 (JP) ............................................ 10-324681

(51) Int. Cl.$^7$ ...................... G01N 33/497; G01N 21/00; C12Q 1/00
(52) U.S. Cl. .......................... 73/23.34; 205/787; 422/83
(58) Field of Search ............................... 73/23.34, 23.2, 73/23.35, 31.03, 31.05; 205/787; 4/321; 417/53, 63, 347; 422/83, 84, 88, 90, 98; 600/532, 342; 436/2, 64

(56) References Cited

U.S. PATENT DOCUMENTS

| 4,772,559 A | * | 9/1988 | Preti et al. ..................... 436/64 |
| 5,541,851 A | | 7/1996 | Sato |
| 5,571,401 A | * | 11/1996 | Lewis ......................... 205/787 |

FOREIGN PATENT DOCUMENTS

| GB | WO 95/32420 | * | 11/1995 | ..................... 436/2 |
| JP | 10227725 | * | 8/1998 | ............ G01N/1/02 |

OTHER PUBLICATIONS

Nakamoto, T. et al; "Active gas/odor sensing system using automatically controlled gas blender and numerical optimization technique" Sensors and Actuators B. Ch B20, No. 2/03 (1994).

Santiago Marco, et al.; "Different strategies for the identification of gas sensing systems"; Sensors and Actuators B. Ch B34 213–223 (1996).

* cited by examiner

Primary Examiner—Hezron Williams
Assistant Examiner—Jay L. Politzer
(74) Attorney, Agent, or Firm—Beyer Weaver & Thomas LLP

(57) ABSTRACT

A device for measurement of an odor component in a sample gas prepares many target gases to be actually measured by a plurality of sensors with different response characteristics, each containing the odor component at a different concentration. Detection signals from these sensors are analyzed by a method of multivariate analysis such as the principal component analysis, and the odor component is characterized on the basis of such an analysis. For preparing the target gases, the sample gas containing the odor component is passed through a collector tube containing an adsorbent which adsorbs this odor component at normal and subnormal temperature and desorbs it when heated. After a specified amount of the odor component is adsorbed to the adsorbent, the tube is heated and an inert gas serving as carrier gas is passed through such that the desorbed odor component is carried to the detectors as a target gas. The concentration of the odor component in such a target gas is controlled by the manner of flow of the carrier gas. In order to obtain a dependable result from such an analysis, response characteristics of each of the sensors may be analyzed by examining the relationship between the outputted detection signal and the concentration of the odor component in the target gas. Only those of the sensors which show a monotonically varying or linear response characteristics may be considered trustworthy and only the detection signals from such trustworthy detectors may be used for the analysis.

18 Claims, 3 Drawing Sheets

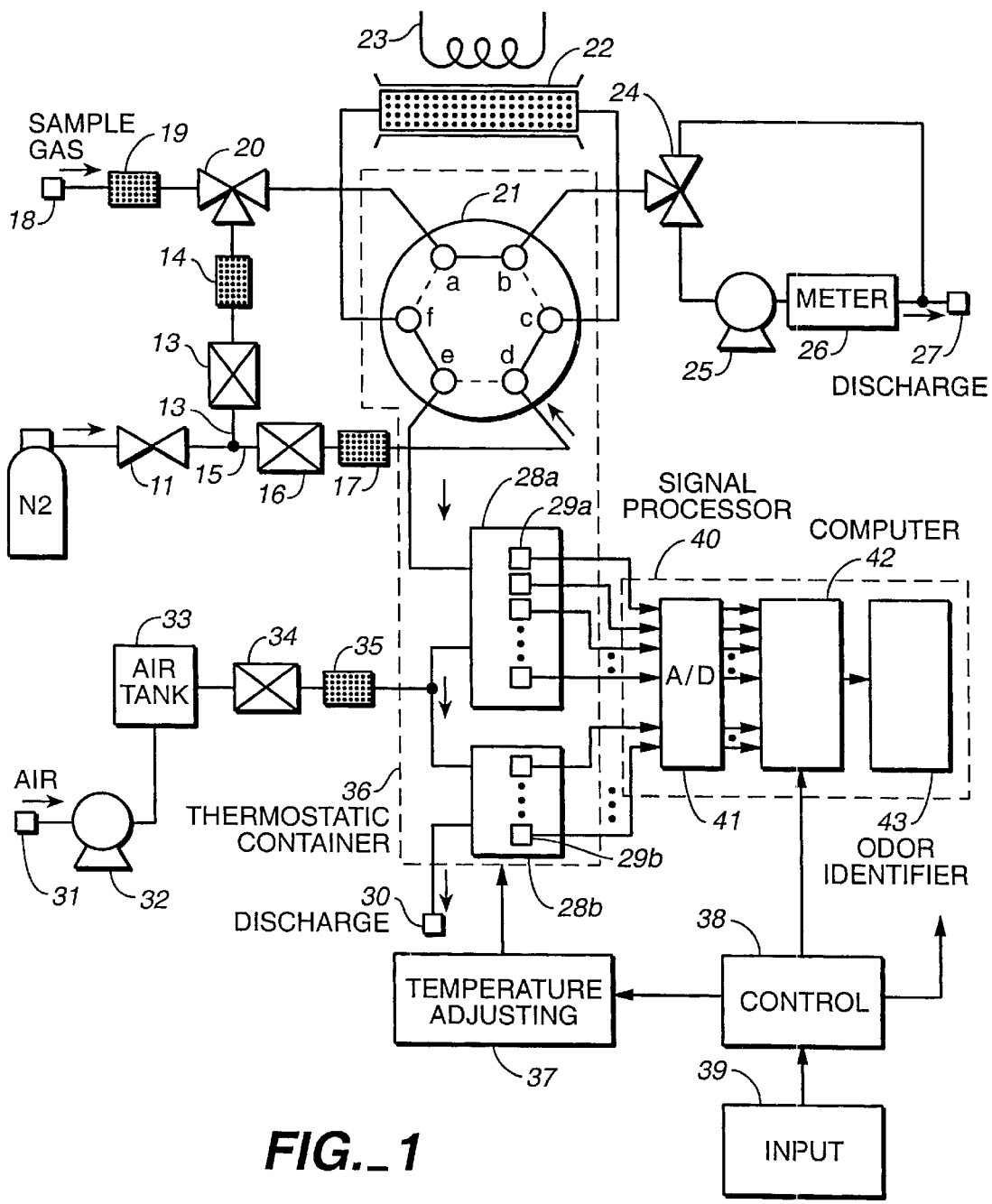
FIG._1

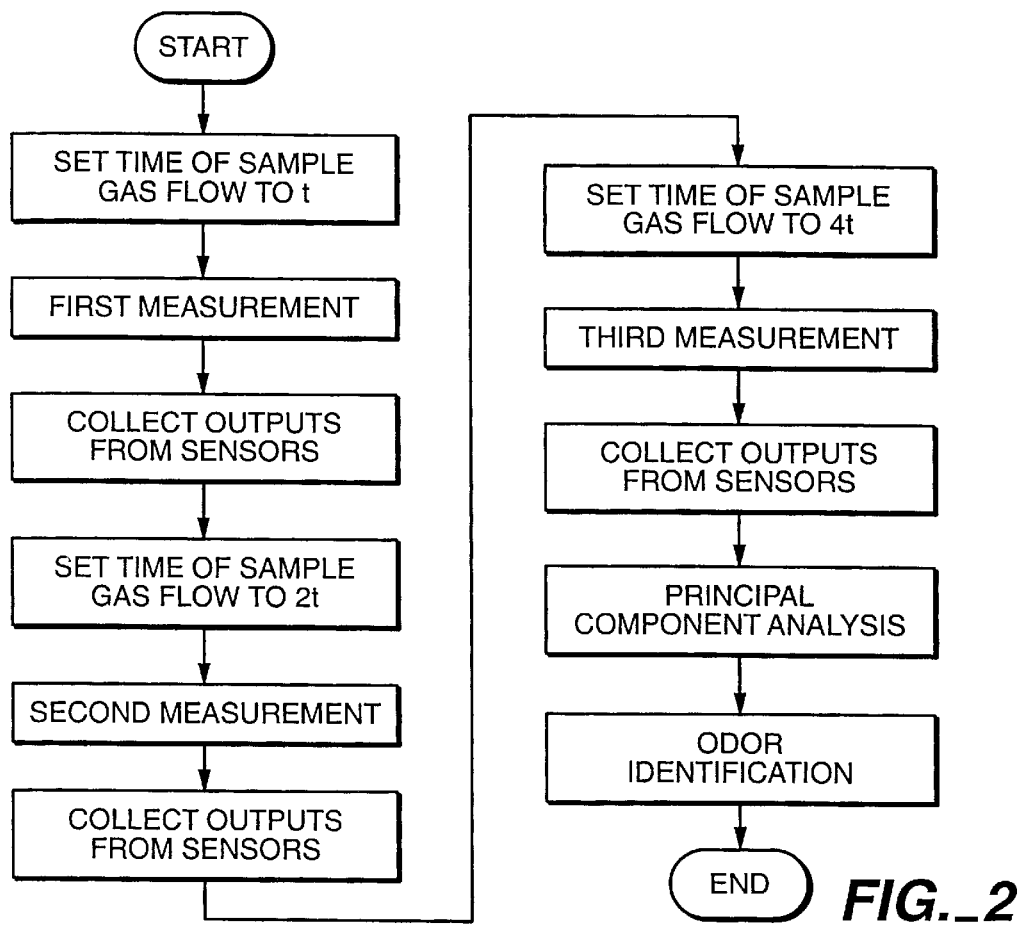
FIG._2
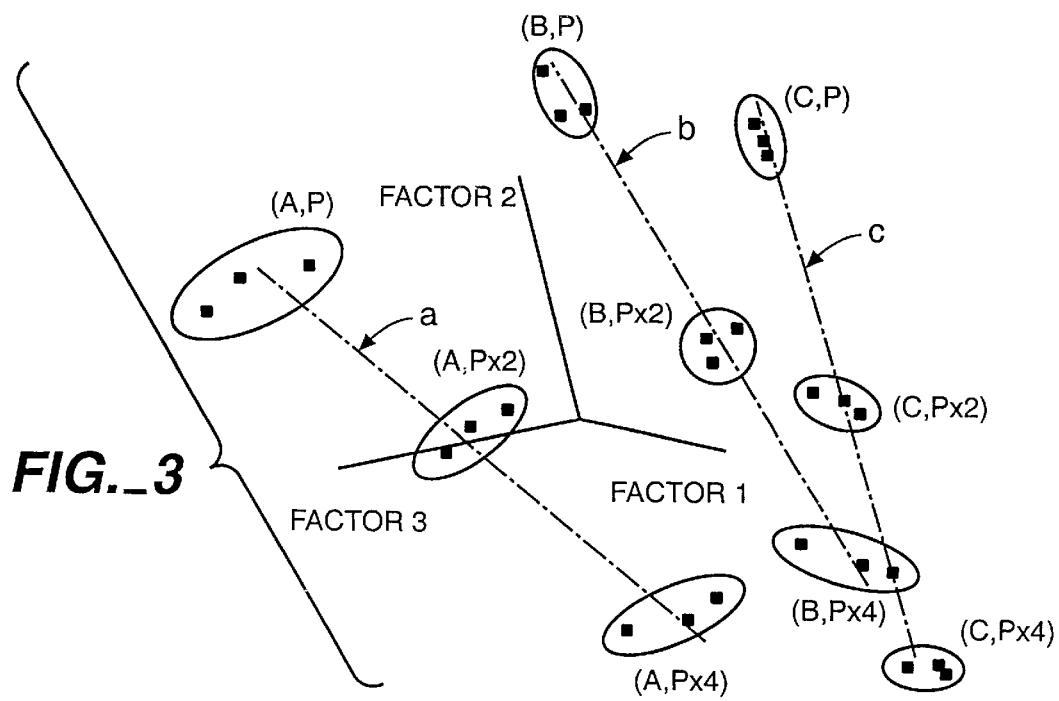
FIG._3

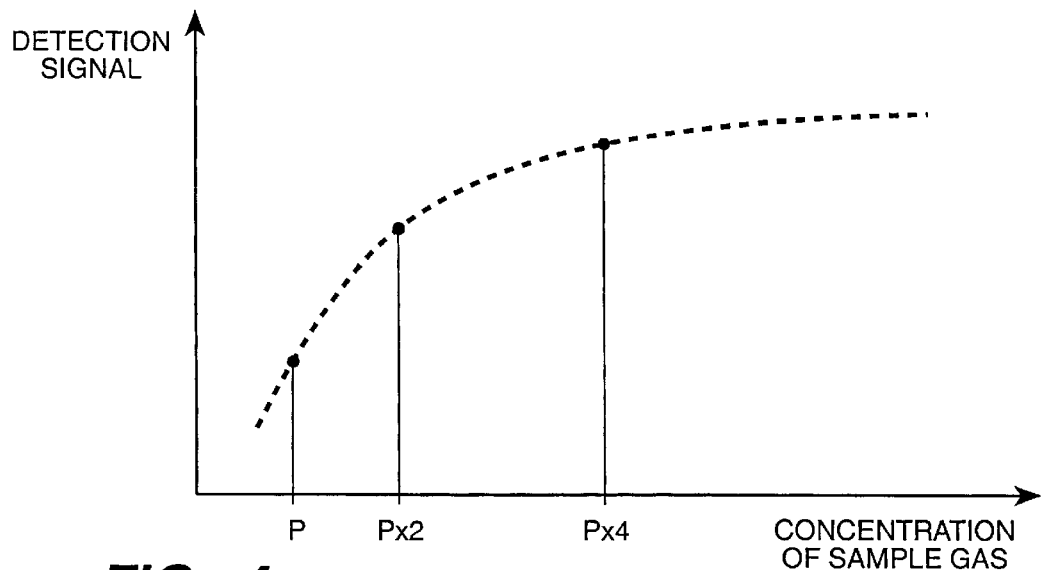
FIG._4
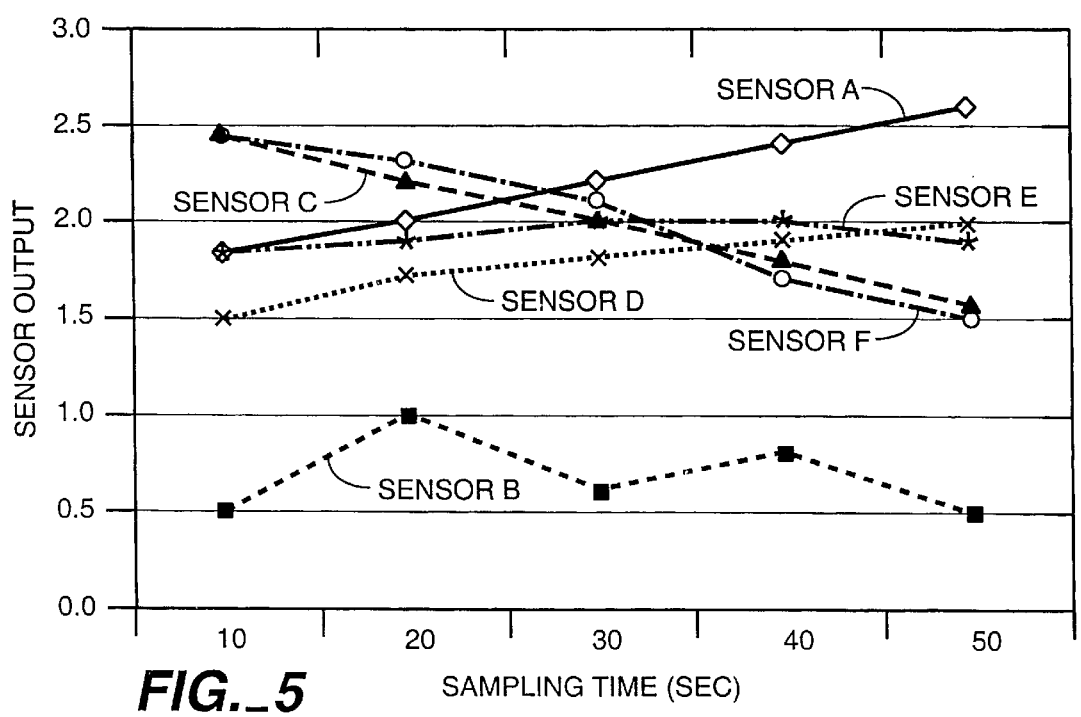
FIG._5

DEVICES FOR MEASURING GASES WITH ODORS

BACKGROUND OF THE INVENTION

This invention relates to devices for measuring odors, gases with odors, or components with odors contained in a sample gas by using odor sensors which are a kind of gas sensors. Such devices according this invention are useful in a large variety of fields of application such as quality control of foods and spices, quantitative analysis of public nuisance involving unpleasant odors, fire detection from a smell of burning matters, and even police works such as tracking and identification of persons in criminal cases and drug inspection.

Odor sensors are adapted to measure changes in themselves electrically or optically caused by odorous components in air or a sample gas which is supplied as they are adsorbed to their odor-sensitive surface. Odor sensors using semiconducting oxides, electrically conductive polymers, a quartz oscillator and a surface acoustic wave (SAW) device are known. Sensors using conductive polymers make use of the change in the conductivity of the polymer as an odorous component is adsorbed. Sensors using semiconducting oxides make use of changes in the resistance of the semiconducting oxide due to the oxidation-reduction reaction of the odorous components in the sample gas. Sensors with an odor-adsorbing film formed on the surface of a quartz oscillator or a SAW device make use of changes in the frequency of oscillation due to change in weight caused by the adsorption of the odorous components. By using odor sensors of these kinds, odor measuring devices can identify, classify and evaluate a given odor, that is, they can determine, when an unknown odorous substance is given, smell or fragrance of what substance its odor most closely resembles, or how to categorize its odor such as the smell of something burning or that the stench of a rotten matter.

Odor sensors using different materials can detect different compounds. Among odor sensors using odor-sensitive films made of conductive polymers, sensors for the detection of different compounds can be obtained by changing the kind of the polymer or the kind of the dopant used for adjusting the conductivity). In general, it is not that each kind of odor sensor can detect only one kind of compounds but most odor sensors can each respond to a number of substances. For analyzing a mixture of many compounds, therefore, a plurality of odor detectors with different sensitivity characteristics are used and the plurality of detection signals from them are analyzed together.

In general, better results of measurement can be expected if a large number of sensors are used. The detection signals from these many sensors may be directly displayed or a technology called chemometrics may be used to carry out a multivariate analysis to measure the odorous compounds. When many sensors are used, however, there are situations wherein some of them turn out to be inappropriate for the detection of odorous components in certain sample gases such that the results of the measurement become worse even if the number of sensors is increased.

An analysis may be carried out, for example, on the basis of ratios between the absolute values of the levels of individual signals obtained from a plurality of sensors and the signal levels of the plurality of sensors. By such a method of analysis, relatively accurate identification is possible if there is a nearly linear relationship between the concentration of the substance and the output level, as is the case with sensors using conductive polymers. In the case of a semiconducting metallic oxide sensor, however, the relationship is non-linear and the analysis is not simple or easy.

SUMMARY OF THE INVENTION

It is therefore an object of this invention to provide a device for measuring gases adapted not to use detection signals from unsuitable sensors such that the accuracy of measurements can be improved.

It is another object of this invention to provide a device for measuring and identifying odors even if sensors with a non-linear response characteristic against concentration are present.

A device for measurement embodying this invention, with which the latter object can be accomplished may be characterized as comprising means for preparing a target gas to be measured from a given sample gas containing an odor component by adjusting concentration of the odor component, a plurality of sensors with different response characteristics for detecting the odor component in the target gas, and a signal processor for analyzing detection signals from the sensors as target gases with different concentrations of this odor component are measured. The odor component is characterized on the basis of an analysis on these detection signals.

For preparing such target gases containing the odor component at different concentrations, the sample gas containing this odor component is passed through a collector tube containing an adsorbent which adsorbs this odor component at normal and subnormal temperatures and desorbs it when heated. After a specified amount of the odor component is thus adsorbed to the adsorbent in the collection tube, the tube is heated and a inert gas is passed through as a carrier gas such that the desorbed odor component is carried to the detectors as a target gas. The concentration of the odor component in such a target gas is controlled by the manner of flow of the inert carrier gas.

The detection signals from the plurality of detectors are analyzed by a suitable method of multivariate analysis such as the principal component analysis. In order to obtain a dependable result from such an analysis, response characteristics of each of the sensors may be analyzed by examining the relationship between the outputted detection signal and the concentration of the odor component in the target gas. Only those of the sensors which show a monotonically varying or linear relationship may be considered trustworthy and only the detection signals from such trustworthy detectors may be used for the analysis.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a schematic gas flow route diagram of a device for measuring odors embodying this invention, combined with a block diagram of its control system with some lines indicative of control relationship omitted for simplifying the diagram;

FIG. 2 is a flow chart for the operation of the device shown in FIG. 1;

FIG. 3 is an example of diagram showing the result of a principal component analysis;

FIG. 4 is a graph which illustrates a relationship between gas concentration and sensor output; and FIG. 5 is another graph which illustrate linear and non-linear relationships between gas concentration and sensor output.

DETAILED DESCRIPTION OF THE INVENTION

The invention is described next by way of examples. FIG. 1 is a schematic gas flow route diagram of a device for measuring odors embodying this invention. A constant-pressure valve 11 is provided at the gas outlet of a nitrogen gas container 10 filled with pure nitrogen gas, and the flow route connected to the outlet of this constant-pressure valve 11 is branched into two (the first and the second) nitrogen gas flow routes 12 and 15. The first nitrogen gas flow route 12 contains a first flow rate controller 13 such as a mass flow controller and a molecular sieve filter 14 for removing impurities. The second nitrogen gas flow route 15 similarly contains a second flow rate controller 16 and a molecular sieve filter 17. A sample gas flow route, connected to a sample gas supply source 18 through a PTFE membrane filter for removing dust, and the first nitrogen gas flow route 12 are selectively connected by a three-way valve 20 (the "first three-way valve") to Port a of a six-way valve 21 with six ports and two positions (shown respectively by solid lines and broken lines). The second nitrogen gas flow route 15 is connected to Port d of the six-say valve 21. A collector tube 22, filled with an adsorbing agent suitable for a target gas with an odor such as carbon-type adsorbent and provided with a heater 23, is connected between Ports c and f. Port b of the six-way valve is connected through another three-way valve 24 (the "second three-way valve") to a discharge outlet 27 either directly or through a flow route which contains a pump 25 and a flow rate meter 26. Port e of the six-way valve 21 is connected to a first flow cell 28a containing a plurality of odor sensors 29a. The outlet on the downstream side of the first flow cell 28a is connected to a second flow cell 28b which also contains a plurality of odor sensors 29b. The outlet on the downstream side of the second flow cell 28b is connected to another discharge outlet 30. The odor sensors 29a of the first flow cell 28a have odor-sensitive films made of electrically conductive polymers having different detection sensitivities against various odor components. The odor sensors 29b of the second flow cell 28b have odor-sensitive films made of semiconducting metallic oxides having different detection sensitivities against various odor components.

Air, sucked in through an air inlet 31 by means of an air pump 32, is stored in an air tank 33 at a high pressure. The outlet of the air tank 33 is connected to the inlet to the second flow cell 28b through a third flow rate controller 34 and a filter 35 comprising active charcoal for removing impurities such that a suitable amount of air can be mixed to the gas flowing from the first flow cell 28a into the second flow cell 28b. Alternatively, it may be so arranged that pure oxygen, instead of air, will be mixed. The use of pure oxygen instead of air is advantageous in that the volume of gas to be mixed can be significantly reduced and hence that the odorous component is less diluted, the sensitivity of detection by the odor sensors 29b being thereby improved.

The six-way valve 21 and the first and second flow cells 28a and 28b are all inside a thermostatic container 36 and kept constantly at a specified temperature by means of a temperature adjusting device 37. Detection signals outputted from the odor sensors 29a and 29b are transmitted to a signal processor 40 for carrying out various processes such as identification and classification of odor components. The signal processor 40 contains an analog-to-digital (A/D) converter 41 for converting detection data into digital data for each odor sensor, a computer 42 for carrying out a principal component analysis (to be described below) which is a kind of multivariate analysis, and an odor identifier 43 for identify the odor of the odor components on the basis of such an analysis. The three-way valves 20 and 24, the six-way valve 21, the pumps 25 and 32, the heater 23, the temperature adjusting device 37 and the signal processor 40 are controlled by a control unit 38 according to a specified program. An input device 39 is connected to the control unit 38 for setting data which may be necessary for the control by the control unit 38.

Operations and functions of various components of the device for measuring odors will be described next.

For collecting odor components, the control unit 38 switches the first three-valve 20 such that the sample gas supply source 18 connects with Port a of the six-way valve 21 and the second three-way valve 24 such that the Port b of the six-way valve 21 connects with the pump 25. The six-way valve 21 is also switched to the position indicated by broken lines in FIG. 1, and the pump 25 is activated. As a result, the suction power of the pump 25 causes the sample gas from the sample gas supply source 18 to have relatively large free particles contained therein such as dust particles removed by the membrane filter 19 and to be introduced into the collector tube 22 (from the left to the right with reference to FIG. 1) through the first three-way valve 20 and the six-way valve 21. The sample gas is thereafter passed through the six-way valve 21 again, the second three-way valve 24, the pump 25 and the flow rate meter 26 to be discharged through the discharge outlet 27. In the meantime, the heater 23 remains switched off.

Since the gas pressure at the outlet of the nitrogen gas container 10 is maintained higher than that at the discharge outlet 30, the nitrogen gas supplied through the second nitrogen gas flow route 15 is passed through the six-way valve 21, the first flow cell 28a and the second flow cell 28b and is discharged through the discharge outlet 30. Thus, the first and second flow cells 28a and 28b are always kept in a nitrogen atmosphere. In the meantime, air from the air tank 33 may be allowed to mix with the nitrogen gas in the second flow cell 28b.

As the sample gas passes through the collector tube 22 as described above, the odor components contained in the sample gas are adsorbed to the adsorbent in the collector tube 22. As long as the ability of the adsorbent to adsorb odor components has not be saturated, the amount of the odor components that are adsorbed is approximately proportional to the total amount of the sample gas which flows through the collection tube 22. If the flow rate is constant, it is proportional to the during of time during which the sample gas passes through the collector tube 22 and if the time of flow is kept constant, the adsorbed amount will be proportional to the flow rate. In reality, however, the molecules of odor components may pass through the collection tube 22 without contacting the adsorbing surface of the adsorbent if the flow rate per unit time is made larger than a certain threshold value. Thus, more accurate results can be expected if the time of flow is changed. According to a preferred embodiment of this invention, therefore, the control unit 38 controls the suction power of the pump 25 such that the detected flow rate by the flow rate meter 26 will remain at a specified value, the time of flow being varied according to a total amount of flow inputted through the input device 39 or a similar parameter.

After the set time for the flow has elapsed, the control unit 38 switches the first three-way valve 20 to connect the first nitrogen gas flow route 12 to Port a of the six-way valve 21 and the second three-way valve 24 to connect Port b of the six-way valve 21 directly to the discharge outlet 27. This will causes the nitrogen gas from the nitrogen gas container 10, instead of the sample gas, to flow through the first nitrogen gas flow route 12, the first three-way valve 20, the six-way valve 21, the collector tube 22, the six-way valve 20 again and the second three-way valve 24 and to be discharge through the discharge outlet 27. By this operation, the portion of the sample gas that remained in this flow route inclusive of the collector tube 22 is pushed by the nitrogen gas out of the flow route to the exterior. Since the heater 23 is not activated during this process, the odor components which became adsorbed earlier to the adsorbent remain adsorbed. Since the nitrogen gas is kept extremely dry, most of the water or water component adsorbed to the adsorbent or attached to the inner walls of the flow route is evaporated and carried out of the flow route. In this manner, removal of moisture can be accomplished to a certain degree.

After the nitrogen gas is passed through the collector tube 22 for an appropriate period of time, the control unit 38 switches the six-way valve 21 to the position indicated by solid lines in FIG. 1, establishing a flow route from the second nitrogen gas flow route 15 through the six-way valve 21, the collector tube 22, the six-way valve again, the first flow cell 28a and the second flow cell 28b to the discharge outlet 30. The heater 23 is activated under this condition such that the collector tube 22 is heated quickly, say, at the speed of about 10° C./second. The odor components adsorbed to the adsorbent inside the collector tube 22 are thereby desorbed and carried away to the first flow cell 28a by the nitrogen gas which is now flowing in the opposite direction (from the right to the left with reference to FIG. 1). If the total amount of nitrogen which flows through the collector tube 22 from the time when the heating of the collector tube 22 is started until the time odor components finish their desorption from the adsorbent is less than the total amount of the sample gas which passed through the collector tube 22 to cause the adsorption of the odor components, the concentration of the odor components in the target gas for the measurement introduced into the first flow cell 28a is higher than that of the sample gas. In other words, although the amount of the odor components adsorbed to the adsorbent in the collector tube 22 is the same, their concentration in the target gas for measurement introduced into the first flow cell 28a can be varied by changing the total amount of nitrogen gas which is caused to pass through the collection tube 22. The flow rate of the nitrogen gas and its time of flow may be held constant such that the concentration of the target gas to be measured can be changed only by controlling the time of flow of the sample gas.

Although the flow route resistance changes according to the temperature of the collector tube 22, the amount of the nitrogen which passes through can be maintained constant if, for example, a mechanical mass flow controller of the variable secondary pressure type is used in the second flow rate controller 16. Since the pressure difference between the inlet and the outlet of such a mass flow controller must be maintained larger than a certain level in order that it can operate normally, the pressure of the constant-pressure valve 11, the inner diameters of the pipes, the flow rate of the air introduced through the third flow rate controller 34, etc. must be selected appropriately such that this pressure difference may be reliably maintained. In this manner, the flow rate of the nitrogen gas can be accurately controlled and the reverse flow of air into the first flow cell 28a can be prevented.

As the target gas for measurement passes through the first flow cell 28a, the odor components are adsorbed to the odor-sensitive films made of electrically conductive polymers of the odor sensors 29a, causing changes in the resistance between the electrodes of the odor sensors 29a. Detection signals indicative of these changes are then transmitted to the signal processor 40.

The air stored in the air tank 33 is passed through the third flow rate controller 34 to have its flow rate and the filter 35 with active charcoal to remove unwanted components which may cause disturbance in the measurement before it is mixed into the target gas which has passed through the first flow cell 28a. Thus, oxygen gas which is part of the air thus introduced is introduced into the second flow cell 28b together with the odor components. The oxygen molecules are adsorbed to the odor-sensitive films comprising semiconducting metallic oxide and cause oxidation-reduction reaction with the molecules of the odor components, affecting the conductivity of the odor sensors 29b. Detection signals caused by this change in resistance between their electrodes are also transmitted to the signal processor 40.

During this measurement, the six-way valve 21, the flow cells 28a and 28b and the flow routes connecting them are maintained by the temperature adjusting device 37 at a temperature somewhat higher than the room temperature such as about 40° C. This is to reduce the effects of variations in the environmental temperature on the odor sensors 29a and 29b and also to prevent compounds with high boiling points from becoming deposited on the inner walls of the flow routes to adversely affect the stability in the detection sensitivity.

Each of the plurality of odor sensors 29a and 29b has different selectivity and response characteristics. For example, it may so happen that a large detection signal can be obtained from a certain odor sensor for a certain odor component while no detection signal can be obtained from the other odor sensors. Thus, the signal sensor 40 identifies or classifies an odor as a whole by carrying out a multivariate analysis of the plurality of detection signals obtained as explained above. There are many known methods of multivariate analysis. A method by so-called principal component analysis (PCA) will be explained below.

After the odor components which have been adsorbed to the adsorbent inside the collector tube 22 are sufficiently completely desorbed as described above, the control unit 38 switches the six-way valve 21 again to the position indicated by the broken lines in FIG. 1 and the temperature inside the thermostatic container 36 is raised to a specified level by means of the temperature adjusting device 37. As clean nitrogen gas thus passes through the first and second flow cells 28a and 28b and the temperature of the odor sensors 29a and 29b rises, the odor components adsorbed to their odor-sensitive films as well as other impurities increase their tendency to be desorbed and are transported by the nitrogen gas to the discharge outlet 30. Thus, the odor-sensitive films of the odor sensors 29a and 29b return to their original conditions, ready to detect odors again.

Next, the flow chart of Fig, 2 is referenced to explain an example of routines for measuring one kind of sample gas.

To start, the user specifies three appropriately different concentration values through the input device 39 although the number of values to be specified need not be three and the user may input some other parameters corresponding to the concentration such as the total amount of the sample gas or the time of flow. Let us assume as an example that the user specifies three concentration values P (in %), 2P and 4P. Although air or oxygen gas is mixed to the target gas to be measured after it passes through the first flow cell 28a according to the embodiment described above with reference to FIG. 1 and hence the concentration of the odor components becomes lower when the target gas passes through the second flow cell 28b, it will be assumed that the flow rate of the nitrogen gas is sufficiently larger than that of air or oxygen and hence that this change in the concentration is negligible. Even in situations where this is not so, the change in concentration as the target gas travels from the first flow cell 28a to the second flow cell 28b can be calculated if the flow rate of air is maintained at a constant level. In the explanation which follows, it will be assumed for the sake of convenience and simplicity that the flow rate of the air which is mixed in is small and that the concentration of the target gas may be regarded invariable.

Once these specified values are received, the control unit 38 calculates the flow times of the sample gas corresponding to these inputted values by using an appropriate formula. If the flow rate of the sample gas (the amount which flows per unit time) and the total amount of the nitrogen gas which flows at the time of desorption are fixed, the concentration of the target gas is proportional to the time of flow of the sample gas. If the time of flow is t (in seconds) corresponding to concentration value P for the target gas to be measured, the times of flow corresponding to concentration values 2P and 4P will be respectively 2t and 4t.

When a measurement is started, the control unit 38 initially sets the time of flow of the sample gas to be t for the adsorption of odor components (Step S1) and the routine described above is carried out (Step S2). In this first measurement, the concentration of the target gas as it flows through the first and second flow cells 28a and 28b is P. The detection signals obtained from the odor sensors 29a and 29b are obtained by the computer 42 through the A/D converter 41 and stored temporarily in its memory device (not shown) (Step S3).

After the routine is completed for the first measurement with the cleaning of the odor sensors 29a and 29b, the control unit 38 sets 2t to be the time of flow of the sample gas through the collector tube 22 (Step S4) and carries out the same measurement routine, causing the target gas at concentration 2P to flow through the first and second flow cells 29a and 29b (Step S5). The detection signals from the odor sensors 29a and 29 are similarly processed by the computer 42 and stored in its memory device (Step S6). After the second measurement is thus completed, the control unit 38 sets 4t to be the time of flow of the sample gas through the collector tube 22 (Step S7) and a third measurement is carried out similarly with the target gas flowing through the first and second flow cells 28a and 28b at still another concentration of 4P (Step S8), the computer 42 ending up by storing another set of data (Step S9).

For each of the three selected values of the concentration of the target gas, the computer 42 carries out a PCA by using the detection signals obtained by the odor sensors 29a and 29b (Step S10). The PCA is carried out by representing a large number of variables in terms of a smaller number of parameter values (referred to as the "factors"), as explained, for example, in "Chemometrics" by Y. Miyashita and S. Sasaki (published by Kyoritsu Publishing Co. (1995)), and can be carried out on a personal computer by using any of various publicly available software programs such as SPSS (Statistical Packages for Social Sciences) sold by SBSS, Inc.

If the number of the factors is set equal to 3, the result of the PCA may be as shown in FIG. 3, represented by points (referred to as the "score points") on a graph (referred to as the "PCA score") having three coordinate axes (referred to as the "factor axes"). If measurements are taken on three target gases at three different concentrations although prepared from the same sample gas, as done in this example, score points usually appear at three mutually separated positions on the PCA score. Although FIG. 2 shows Step S10 as coming after Step S9 for the convenience of description, the computer 42 is not required to wait until detection signals from the third measurement are processed and stored in order to start the PCA. After detections signals from each measurement are processed and stored, The computer 42 may start the PCA for that set of data corresponding to one of the selected concentration values.

After the PCA calculations of data corresponding to all selected concentration values are finished, the odor components are identified (Step S11) as follows by the odor identifier 43. For the convenience of description, let us assume that sample gases of three kinds A, B and C have been measured and that the second flow cell 28b contains six odor sensors 29b each having an odor-sensitive film comprising a semiconducting metal oxide. In view of the variations in the results of measurement, let us assume that each sample gas was measured three times at each of the concentration values P, 2P and 4P of the target gas.

FIG. 3 shows an example of PCA score thus obtained. On a PCA score, score points which are closely related usually appear close to one another. The three score points from three repeated measurements corresponding to the same sample gas and the same concentration value are found to be located mutually close together. Each set of parentheses associated with a group of such score points that are close together indicates the associated sample gas and the corresponding concentration value.

Groups of score points associated with the same sample gas but corresponding to different concentration values are farther separated but it is usually possible to draw a straight line connecting these groups of score points, as shown by chain lines a, b and c in FIG. 3, corresponding respectively to the groups associated with sample gases A, B and C. These lines are herein referred to as the concentration-dependence lines. It is on the basis of the positional relationship of these concentration-dependence lines that the odor identifier 43 identifies similarities among odors. If the concentration-dependence lines of two kinds of sample gases are approximately in a one-on-top-of-the-other relationship, for example, it may be concluded that their odors belong to the same category. If their concentration-dependence lines do not exactly lie one on top of the other but if they are parallel and relatively close to each other, it may likewise be concluded that their odors are somewhat similar or of the same type. By contrast, if they are far apart or oriented in completely different directions, it may be concluded that the odors are of totally different kinds. Because the three concentration-dependence lines a, b and c shown in FIG. 3 are relatively far apart, the sample gases A, B and C, or the odor components contained in them, may be said to have different kinds of odors.

Identifications of this kind can be made more precisely if a larger number of odor sensors are used and if odor sensors with higher selectivity characteristics are used. If sensors with relatively lower selectivity characteristics are used, this means that they have similar response characteristics against many similar kinds of components and, although it can be concluded that two odors are similar to each other if the corresponding concentration-dependence lines are one on top of each other, it is difficult even in such a case to conclude that these components are identical. If sensors with high selectivity characteristics are used, on the other hand, it can be concluded in such a situation that the two corresponding sample gases contain the same odor component.

Although FIG. 3 shows three straight concentration-dependence lines, concentration-dependence lines are not always straight. This means that it is preferable to select three or more concentration levels at which measurements of the same sample gas are to be made.

Next, FIG. 4 is referenced to explain a method of analysis for correcting a non-linear dependence of odor sensors on concentration when detection signals therefrom are used as described above in order to identify odors more correctly. As shown in FIG. 4 as an example, the relationship between the concentration and the detection signal for each odor sensor should be known and hence it ought to be possible to approximate this known functional relationship by an equation. Since such an approximating equation should contain parameters which depend on the odor component, it should be possible to "solve" the equation and to thereby determine these parameters from experimentally determined points on the curve such as the one shown by a broken line in FIG. 4. Odors may be identified by comparing these parameter.

For this method, many already proposed approximating equations can be used. For example, P. K. Clifford, et al. have proposed in "Sensors and Actuators, 3 (1982/1983)" the following approximating equation for sensors comprising semiconducting metallic oxides:

$$(R/R_0)^{-(1/k)} = (1+KG^n)/O \quad (1)$$

where R is the detected value of sensor resistance, $R_0$ is the sensor resistance in air (initial value), G is the concentration of the target gas being measured, O is the oxygen concentration and k, K and n are constants. The initial value of resistance $R_0$ can be preliminarily determined. The oxygen concentration O may be considered known because it can be readily determined from the flow rate of air or oxygen gas which is mixed in. Thus, if sensor resistance R is measured at different value of the target gas concentration and if these values are substituted into Formula (1), the constant k, K and n can be determined.

As another example, R. K. Srivastava, et al. have proposed the following substituting equation in "Sensors and Actuators, B21 (1994)":

$$\log(R/R_0) = -BG^b \quad (2)$$

where R and $R_0$ are as defined above, and the constants to be determined are B and b.

It now goes without saying that many other similar approximating equations can be used. It is preferable in fact to use different approximating equation for different kinds of odor sensors. Although some of these equations may contain a rather large number of parameters, not all of these parameters are necessarily dependent on the kind of odor component. In other words, some of many parameters may be regarded as constants and hence it may not be necessary to increase the number of concentration values at which measurements should be taken. It should also be noted that some of these equations may be applicable only within a limited range of gas concentration. Such limitations should be preliminarily recorded through the input device 39. In summary, many modifications and variations are possible on the basis of the disclosure given above. The right-hand side of (2), for example, may be replaced by $G^h/(1+G^h)$ or $\{G/(1+G)\}^h$ where h is a single parameter. The concentration of the target gas need not be set desired levels by adjusting the flow time of the sample gas of flow but may be by some other parameter.

There is still another approach to the problem of improving the reliability of analysis by using detection signals from only reliable ones of the plurality of odor sensors by determining which of the sensors have linear response characteristics, or a monotonically increasing or decreasing relationship between the detection signal and the concentration of the target gas because data processing is easier if such a relationship exists.

Signal processing according to this approach will be explained next with reference to FIG. 1 again for the sake of convenience. For the sake of convenience again, let us assume that a single sample containing a certain organic acid was given and that the device as illustrated in FIG. 1 was operated as described above to measure the odor component of this organic acid by using six odor sensors (identified below as A, B, C, D, E and F) and by changing the concentration of the target gas to be measured, that is, by preparing from the sample gas different target gases with different concentrations of the odor component. Let us further assume that these target gases with different concentrations were prepared by changing the flow time of the sample gas through the collector tube 22, as explained above. The measured detection signals may be as shown in FIG. 5 wherein the vertical axis represents the sensor output in arbitrary units and the horizontal axis represents the sampling time, representing the concentration of the target gas.

The odor identifier 43 of the signal processor 40 according to this embodiment of the invention, upon reviewing a result of measurements as represented in FIG. 5, recognizes that the relationship shown in the graph is linear only with sensors A and C and transmits only the detection signals from these two sensors as being reliable, or easy to process. In other words, odor identification is done on the basis of detection signals only from those sensors with a clear relationship between the signal output and the concentration and hence the accuracy of analysis can be improved.

If the purpose of analysis is odor identification not including quantitative analysis, sensors with a monotonically increasing or decreasing relationship between the sensor output and the concentration may be included. In the Example of FIG. 5, sensor C shows a monotonically decreasing relationship and sensor D shows a monotonically increasing relationship although neither relationship is linear, while sensors B and E do not show such a monotonically changing relationship. Thus, it may be decided to transmit detection signals from sensors A, C, D and F, excluding those from sensors B and E, to be included in the analysis.

In summary, many modifications and variations are possible within the scope of the invention. The type of odor sensors is not intended to limit the scope of the invention. Besides sensors comprising semiconductor metallic oxides and electrically conductive polymers, those having an odor-sensitive film formed on the surface of a quartz oscillator or a surface acoustic wave device may be used. The device need not necessarily be of a type using a collector tube. A device adapted to prepare target gases with specified concentrations of odor component from a given sample gas may be used instead. In summary, all such modifications and variations that may be apparent to a person skilled in art are intended to be included within the scope of the invention.

What is claimed is:

1. A device for measuring odors, said device comprising:
    target gas preparing means for preparing target gases to be measured from a given sample gas containing an odor component by varying concentration of said odor component in said target gases;

a plurality of sensors with different response characteristics to concentration for detecting said odor component in said target gases; and signal processing means for analyzing detection signals which said sensors output by measuring target gases prepared by said target gas preparing means and having different concentrations of said odor component, said signal processing means thereby characterizing said odor component.

2. The device of claim 1 wherein said target gas preparing means prepares said target gases by causing said odor component of said sample gas to be adsorbed to an adsorbent and thereafter causing said adsorbed odor component to be desorbed into an inert gas.

3. The device of claim 1 wherein said target gas preparing means comprises:

a collector tube containing an adsorbent which adsorbs said odor component at normal and subnormal temperatures and desorbs said adsorbed odor component when heated;

a heater for heating said adsorbent;

gas flowing means for causing said sample gas and a inert gas selectively through said collector tube; and flow control means for setting a parameter for operating said gas flowing means so as to prepare target gases with said different concentrations of said odor component.

4. The device of claim 2 wherein said target gas preparing means comprises:

a collector tube containing said adsorbent, said adsorbent adsorbing said odor component at normal and subnormal temperatures and desorbing said adsorbed odor component when heated;

a heater for heating said adsorbent;

gas flowing means for causing said sample gas and said inert gas selectively through said collector tube; and flow control means for setting a parameter for operating said gas flowing means so as to prepare target gases with said different concentrations of said odor component.

5. The device of claim 3 wherein said parameter is related to total amount of said sample gas to be passed through said collector tube.

6. The device of claim 1 further comprising a control unit which causes said target gas preparing means to sequentially generate target gases containing said odor component at specified different concentrations.

7. The device of claim 2 further comprising a control unit which causes said target gas preparing means to sequentially generate target gases containing said odor component at specified different concentrations.

8. The device of claim 3 further comprising a control unit which causes said target gas preparing means to sequentially generate target gases containing said odor component at specified different concentrations by sequentially changing said parameter.

9. The device of claim 1 wherein said signal processing means calculates from said detection signals indicators for characterizing said odor component in said target gases.

10. The device of claim 1 wherein said signal processing means include computing means for carrying out a multivariate analysis of said detection signals outputted from said plurality of sensors.

11. The device of claim 10 wherein said computing means carries out said multivariate analysis by principal component analysis.

12. The device of claim 10 further comprising odor identifying means for characterizing said odor component from results of said multivariate analysis by said computing means based on detection signals outputted from said plurality of detectors by measuring target gases prepared by said target gas preparing means and containing said odor component at different concentrations.

13. The device of said 1 wherein said signal processing means includes response detecting means for detecting for each of said plurality of sensors whether the concentrations of said odor component in said target gases and said detection signals are in monotonically changing relationship, in linearly changing relationship or otherwise.

14. The device of said 13 wherein said signal processing means further includes sensor selecting means for selecting only those of said plurality of sensors for which said response detecting means detected that the concentrations of said odor component in said target gases and said detection signals are in monotonically changing or linearly changing relationship and allowing only those of said detection signals from said selected sensors to be used by said signal processing means in characterizing said odor component.

15. The device of claim 6 wherein said signal processing means include computing means for carrying out a multivariate analysis of said detection signals outputted from said plurality of sensors.

16. The device of claim 15 further comprising odor identifying means for characterizing said odor component from results of said multivariate analysis by said computing means based on detection signals outputted from said plurality of detectors by measuring target gases prepared by said target gas preparing means and containing said odor component at different concentrations.

17. The device of claim 6 wherein said signal processing means includes response detecting means for detecting for each of said plurality of sensors whether the concentration of said odor component in said target gas gases and said detection signals are in monotonically changing relationship, in linearly changing relationship or otherwise.

18. The device of said 17 wherein said signal processing means further includes sensor selecting means for selecting only those of said plurality of sensors for which said response detecting means detected that the concentration of said odor component in said target gases and said detection signals are in monotonically changing or linearly changing relationship and allowing only those of said detection signals from said selected sensors to be used by said signal processing means in characterizing said odor component.

* * * * *